United States Patent [19]
Bergstrom et al.

[11] Patent Number: 6,148,272
[45] Date of Patent: Nov. 14, 2000

[54] SYSTEM AND METHOD FOR RADIATION DOSE CALCULATION WITHIN SUB-VOLUMES OF A MONTE CARLO BASED PARTICLE TRANSPORT GRID

[75] Inventors: Paul M. Bergstrom; Thomas P. Daly; Edward I. Moses; Ralph W. Patterson, Jr.; Alexis E. Schach von Wittenau; Dewey N. Garrett, all of Livermore; Ronald K. House, Tracy; Christine L. Hartmann-Siantar, Livermore, all of Calif.; Lawrence J. Cox, Los Alamos, N. Mex.; Donald H. Fujino, San Leandro, Calif.

[73] Assignee: The Regents of the University of California, Oakland, Calif.

[21] Appl. No.: 09/238,297

[22] Filed: Jan. 28, 1999

[51] Int. Cl.$^7$ ....................................................... A61N 5/10
[52] U.S. Cl. ........................................ 702/179; 250/363.04
[58] Field of Search .............................. 702/179; 378/65, 378/82, 83; 250/252.1, 363.04, 370.07, 390.03

[56] References Cited

U.S. PATENT DOCUMENTS

| 5,341,292 | 8/1994 | Zamenhof | 364/413.13 |
| 5,418,715 | 5/1995 | Deasy | 364/413.26 |
| 5,787,888 | 8/1998 | Schotland | 128/653.1 |
| 5,844,241 | 12/1998 | Liu et al. | 250/363.04 |
| 5,870,697 | 2/1999 | Chandler et al. | 702/179 |

OTHER PUBLICATIONS

Zubal et al., "High Resolution Anthropomorphic Phantom for Monte Carlo Analysis of Internal Radiation Sources", IEEE, 1990.

Sato et al., "A New Method for Photon Transport in Monte Carlo Simulation", IEEE, 1999.

Miyazawa et al., "Visualization of 3D Medical Images for Radiotherapy Planning", IEEE, 1992.

*Primary Examiner*—Patrick Assouad
*Attorney, Agent, or Firm*—Lloyd E. Dakin Jr; Alan H. Thompson

[57] ABSTRACT

A system and method is disclosed for radiation dose calculation within sub-volumes of a particle transport grid. In a first step of the method voxel volumes enclosing a first portion of the target mass are received. A second step in the method defines dosel volumes which enclose a second portion of the target mass and overlap the first portion. A third step in the method calculates common volumes between the dosel volumes and the voxel volumes. A fourth step in the method identifies locations in the target mass of energy deposits. And, a fifth step in the method calculates radiation doses received by the target mass within the dosel volumes. A common volume calculation module inputs voxel volumes enclosing a first portion of the target mass, inputs voxel mass densities corresponding to a density of the target mass within each of the voxel volumes, defines dosel volumes which enclose a second portion of the target mass and overlap the first portion, and calculates common volumes between the dosel volumes and the voxel volumes. A dosel mass module, multiplies the common volumes by corresponding voxel mass densities to obtain incremental dosel masses, and adds the incremental dosel masses corresponding to the dosel volumes to obtain dosel masses. A radiation transport module identifies locations in the target mass of energy deposits. And, a dose calculation module, coupled to the common volume calculation module and the radiation transport module, for calculating radiation doses received by the target mass within the dosel volumes.

41 Claims, 7 Drawing Sheets

SYSTEM AND METHOD FOR RADIATION DOSE CALCULATION WITHIN SUB-VOLUMES OF A MONTE CARLO BASED PARTICLE TRANSPORT GRID

REFERENCE TO PROVISIONAL APPLICATION TO CLAIM PRIORITY

A priority date for this present U.S. patent application has been established by prior U.S. Provisional Patent Application, Serial No. 60/108,092, entitled "System and Method for Radiation Dose Calculation Within Sub-Volumes of a Monte Carlo Based Particle Transport Grid," filed on Nov. 11, 1998 by inventors Bergstrom et al.

CROSS-REFERENCE TO RELATED APPLICATIONS

This application relates to and incorporates by reference U.S. patent application Ser. No. 08/610,917, now U.S. Pat. No. 5,870,697 entitled "Calculation of Radiation Therapy Dose Using All Particle Monte Carlo Transport," filed on Mar. 5, 1996, by Chandler et al. This related application is commonly assigned to The Regents of the University of California.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention relates generally to systems and methods for radiation dose calculation, and more particularly for radiation dose calculation within sub-volumes of a Monte Carlo based particle transport grid.

2. Discussion of Background Art

Successful human radiation therapy consists of three critically linked components: patient evaluation, treatment planning, and treatment delivery. In the last several decades, technology for patient evaluation and treatment delivery have improved dramatically, providing an array of imaging (such as CT or MRI scans) and treatment delivery devices that has, so far, outmatched the radiation therapy field's ability to fully utilize them. Full realization of the benefits of these advances requires sophisticated, accurate treatment planning.

A critical part of treatment planning is an accurate determination of dose distribution in the patient. An International Commission on Radiation Units and Measurements (ICRU) paper entitled, "Use of computers in external beam radiotherapy procedures with high-energy photons and electrons," ICRU Report 42 (1987) recommends a dose calculation accuracy goal of 2% in low dose gradient regions. Currently, however, dose calculation errors in heterogeneous media range from 3% to more than 10%, as discussed in articles by M. E. Masterson et al., entitled "Interinstitutional experience in verification of external photon dose calculations," Int. J. Oncology Biol. Phys. 21 37–58 (1991); by K. Ayyangar et al., entitled "Experimental verification of a three-dimensional dose calculation algorithm using a specially designed heterogeneous phantom," Med. Phys. 21 (2) 325–329 (1993); by C. Hurkmans et al., entitled "Limitations of a pencil beam approach to photon dose calculations in the head and neck region," Radiotherapy and Oncology 39 74–80 (1995); and by T. Knöös et al., entitled "Limitations of a pencil beam approach to photon dose calculations in lung tissue," Phys. Med. Biol. 40 1411–1420 (1995)).

Convolution and superposition algorithms can be significantly more accurate that older methods, but increase computation time considerably. Convolution and superposition algorithms are discussed in articles by A. Boyer and E. Mok, entitled "A photon dose distribution model employing convolution calculations," Med. Phys. 12 169–177 (1985); by T. R. Mackie et al., entitled "A convolution method of calculating dose for 15 MV x rays," Med. Phys. 12 188–196 (1985); by R. Mohan et al., entitled "Differential pencil beam dose computation model for photons," Med. Phys. 13 64–73 (1986); by A. Ahnesjö et al., entitled "Calculation and application of point spread functions for treatment planning with high energy photon beams," Acta Oncol. 26 49–56 (1987); by R. Mohan and C. Chui, "Use of fast Fourier transforms in calculating dose distribution of irregularly shaped fields for three-dimensional treatment planning," Med. Phys. 14 70–77 (1987); by P. E. Metcalfe et al., entitled "Modeling polychromatic high energy photon beams by superposition," Aust. Phys. Eng. Sci. Med 12 138–148 (1989); and by P. W. Hoban et al., entitled "Superposition dose calculations in lung for 10 MV photon," Aust. Phys. Eng. Sci. Med 13 81–92 (1990).

Monte Carlo dose calculation techniques, however, are widely accepted as a preferred method for dose calculation. Monte Carlo techniques are capable of accurately computing dose under almost all circumstances. For related articles authored by R. Mohan, entitled "Dose Calculations for Radiation Treatment Planning," in T. M. Jenkins, W. R. Nelson, and A. Rindi, eds., Monte Carlo Transport of Electrons and Photons, 549–471 (1988); by D. W. O. Rogers and A. F. Bielajew, entitled "Monte Carlo techniques of electron and photon transport for radiation dosimetry," in The Dosimetry of Ionizing Radiation, Vol. III, edited by K. R. Kase, B. E. Bjarngard, and R. H. Attix (academic, New York (1990), pp. 427–539; and by T. R. Mackie, entitled "Applications of the Monte Carlo method in radiotherapy," in The Dosimetry of Ionizing Radiation, Vol. III, edited by K. R. Kase, B. E. Bjarngard, and R. H. Attix (academic, New York (1990), pp. 541–620. Monte Carlo techniques can also be applied toward weapons modeling and understanding the irradiation of food.

Unfortunately, Monte Carlo calculations for a single treatment plan can take days or sometimes weeks. See A. E. Nahum, "Overview of Photon and Electron Monte Carlo," in T. M. Jenkins, W. R. Nelson, and A. Rindi, eds., Monte Carlo Transport of Electrons and Photons, 3–20 (1988). Monte Carlo algorithms currently require expert users to set up and are also very slow to execute. In addition, currently, Monte Carlo algorithms are optimized for calculating doses over an entire CT or MRI scan. Thus, when a dose calculation over only a small portion of the CT or MRI scan is desired, general purpose Monte Carlo algorithms provide much more information than is necessary, at a considerable cost in computation time.

In response to the concerns discussed above, what is needed is a system and method for radiation dose calculation that overcomes the problems of the prior art.

SUMMARY OF THE INVENTION

The present invention is a system and method for radiation dose calculation within sub-volumes of a Monte Carlo based particle transport grid. The present invention is applicable to many problems in which energy or dose calculations are required. Within the method of the present invention, voxel volumes enclosing a first portion of the target mass are received. A second step in the method defines dosel volumes which enclose a second portion of the target mass and overlap the first portion. A third step in the method calculates common volumes between the dosel volumes and the voxel volumes. A fourth step in the method identifies locations in the target mass of energy deposits. And, a fifth step in the method calculates radiation doses received by the target mass within the dosel volumes.

Within the system of the present invention, a common volume calculation module inputs voxel volumes enclosing a first portion of the target mass, inputs voxel mass densities corresponding to a density of the target mass within each of the voxel volumes, defines dosel volumes which enclose a second portion of the target mass and overlap the first portion, and calculates common volumes between the dosel volumes and the voxel volumes. A dosel mass module, multiplies the common volumes by corresponding voxel mass densities to obtain incremental dosel masses, and adds the incremental dosel masses corresponding to the dosel volumes to obtain dosel masses. A radiation transport module identifies locations in the target mass of energy deposits. And, a dose calculation module, coupled to the common volume calculation module and the radiation transport module, for calculating radiation doses received by the target mass within the dosel volumes.

Using the system and method of the present invention, a general purpose Monte Carlo algorithm for radiation dose calculation is effectively modified into a special purpose algorithm which performs dose calculation over a smaller sub-volume than specified by a CT or MRI scan. The dosel volume enables dose calculations to be performed at a location and a resolution requested by a user. With the dosel volume, dose calculation resolution is no longer tied to a CT or MRI scan slice spacing, which can be irregular and much coarser than may be desirable in a head-to-foot direction of a patient, while being too fine in a transverse (across-the-body) direction.

Depending upon a size of the dosel volume, calculations may converge with fewer Monte Carlo energy depositions. In addition, the present invention uses variance reduction techniques to track particles significantly faster than current analysis techniques, since users can define a dose reporting region smaller than a complete CT or MRI scan.

These and other aspects of the invention will be recognized by those skilled in the art upon review of the detailed description, drawings, and claims set forth below.

DETAILED DESCRIPTION OF THE PREFERRED EMBODIMENT

Figure 1:
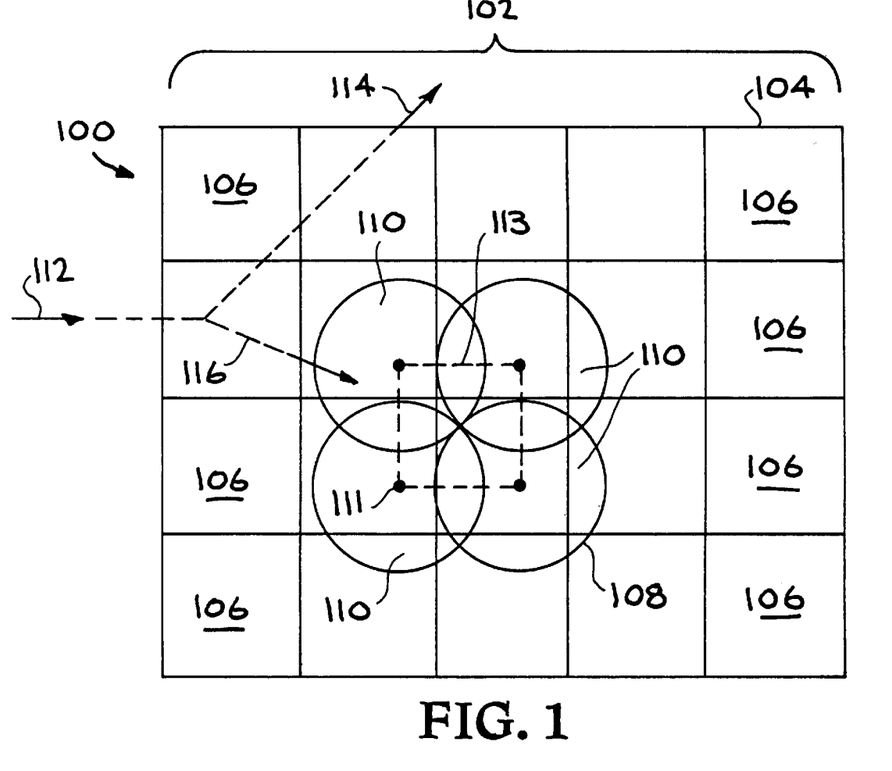
FIG. 1 is a pictorial diagram of a system for radiation dose calculation within sub-volumes of a Monte Carlo based particle transport grid according to the present invention.

FIG. 1 is a pictorial diagram 100 of a system for radiation dose calculation within sub-volumes of a Monte Carlo based particle transport grid according to the present invention. A radiation dose is a well known term of art, defined as an amount of energy per unit mass deposited within a target mass (not shown). There are three basic steps to calculating a radiation dose received by the target mass. A first step consists of identifying a sub-volume of interest in the target mass for which the radiation dose is to be calculated. Second, radiation transported through the target mass is monitored and an amount of energy deposited within the sub-volume is recorded. And third, the radiation dose is calculated for the sub-volume by dividing the amount of energy deposited within the sub-volume by that portion of the target mass contained within the sub-volume.

The diagram 100 shows a set of two-dimensional representations of sub-volumes 102 which overlay the target mass. The target mass is a structure, such as a tumor in a cancer patient, which is to receive a radiation dose. The set of two-dimensional representations of sub-volumes are shown in FIG. 1 for simplicity, however, a real world target mass is three-dimensional, and so the present invention is discussed in three-dimensions.

The set of sub-volumes 102 are arranged in a voxel (i.e. volume element) grid 104. Voxel and voxel grid are common terms well known by those skilled in the art. The voxel grid 104 can alternatively be called a particle transport grid. The voxel grid 104 is defined when a CT or MRI scan is taken of the target mass. The CT or MRI scan defines rectangular parallelepipeds within the voxel grid 104 called voxels 106. Each of the voxels 106 has a constant mass density and atomic composition which can be assigned from the CT or MRI scan.

Currently, Monte Carlo based radiation dose calculation systems calculate a radiation dose for each and every voxel. Since Monte Carlo calculations take a significant amount of computing power, calculating a radiation dose for each and every voxel is inordinately time consuming, especially if a user requires radiation dose information over a smaller area.

In response, the present invention permits the user to define a dosel grid 108, covering a region of interest in the target mass for which the user requires radiation dose information. Typically, a volume of the target mass defined by the dosel grid 108 will be smaller than that defined by the voxel grid 104, although the dosel grid 108 could be larger. When the dosel grid 108 is smaller, however, the Monte Carlo calculations will take significantly less time and computational power to complete. Also, since the dosel grid 108 is independent of the voxel grid 104, the user has a greater level of flexibility when specifying the region of interest for the Monte Carlo dose calculations. Also, a ratio of grid spacing between the dosel and voxel grids can be changed at the user's discretion. Thus, the dosel grid 108 also enables a user to perform dose calculation of varying resolution, whereas a resolution of the voxel grid 104 is fixed once the CT or MRI scan is taken.

The dosel grid 108 comprises a set of dosels 110. Each dosel has a dosel volume which is centered about a dosel grid point 111. The dosels 110 can be of any shape, including spherical, cubical, or tetrahedral. Dosels 110 may also have varying degrees of overlap. In the preferred embodiment, the dosels 110 are of uniform size and spacing. A radius of each of the dosels 110 is defined such that dosels 110 on diagonal corners of a unit cell 113 of the dosel grid 108 just touch. Thus, when viewed in three dimensions, the unit cell 113 is preferably a cube. Dosels within the dosel grid 108 overlap so that subsequent energy depositions can be over-sampled, yielding faster convergence times.

After the dosel volumes are defined, a dosel mass is calculated for each dosel based on the CT or MRI scan mass density data for those voxels which each dosel overlaps. A closed form solution is presented infra. A particle transport beam 112, directed toward the target mass, delivers radiation. The particle transport beam 112 may consist of any number of types of subatomic particles, such as photons, neutrons, protons, alpha particles, electrons, and positrons. As the particle transport beam 112 interacts with the target mass, an incident particle in the beam 112 may be scattered 114 and release an electron 116 or positron. The present invention employs variance reductions techniques to selectively track, using Monte Carlo algorithms, those incident and scattered particles, electrons, and positrons which are most likely to pass through the region of interest in the target mass as defined by the dosel grid 108. Incident and scattered particles, electrons, and positrons which are not likely to pass through the region of interest in the target mass are not tracked. Through selective tracking, a significant saving in computational power requirements and time is achieved. Details of dosel grid 108 set-up, dosel mass calculation, radiation transport (i.e. particle tracking), and dose calculation are now presented.

Figure 2:
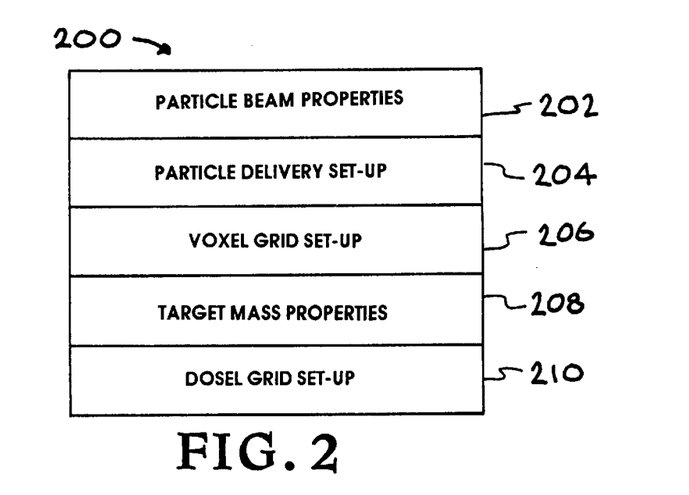
FIG. 2 is a block diagram of a set of input parameters.

FIG. 2 is a block diagram of a set of input parameters 200. The input parameters 200 include particle beam properties 202; particle delivery set-up 204; voxel grid set-up 206; target mass properties 208; and dosel grid set-up 210. The particle beam properties 202 include types of particles in the particle beam 112, and various other well known atomic and nuclear data which quantify the particle beam 112. The particle delivery set-up 204 includes parameters on particle beam alignment and a total number of beams. The voxel grid set-up 206 specifies an arrangement and spacing of the voxel grid 104. The target mass properties 208, such as mass density and atomic composition of the target mass within each of the voxels 106 are derived from the CT or MRI scan data. For purposes of invention discussion, the dosels 110 will be assumed to be spheres, however, those skilled in the art will recognize that complexity of the mathematics for calculating overlapping volumes decreases substantially if the dosels 110 are cubes.

The dosel grid set-up 210 specifies various details which geometrically layout the dosels 110 within the dosel grid 108, including: a spherical radius for each of the dosels 110; a starting point (x, y, z) for a center of the dosels 110 within the target mass; and an arrangement (ix, jy, kz) of the dosels 110 about the starting point. i, j, and k are variables specifying a position of each sphere within a Cartesian coordinate system. The arrangement can be a single sphere centered about the starting point (1x, 1y, 1z); a line of spheres (ix, 1y, 1z); a plane of spheres (ix, jy, 1z); or a volume of spheres (ix, jy, kz). Thus the dosel grid 108 can cover any desired volume within the target mass.

Figure 3A:
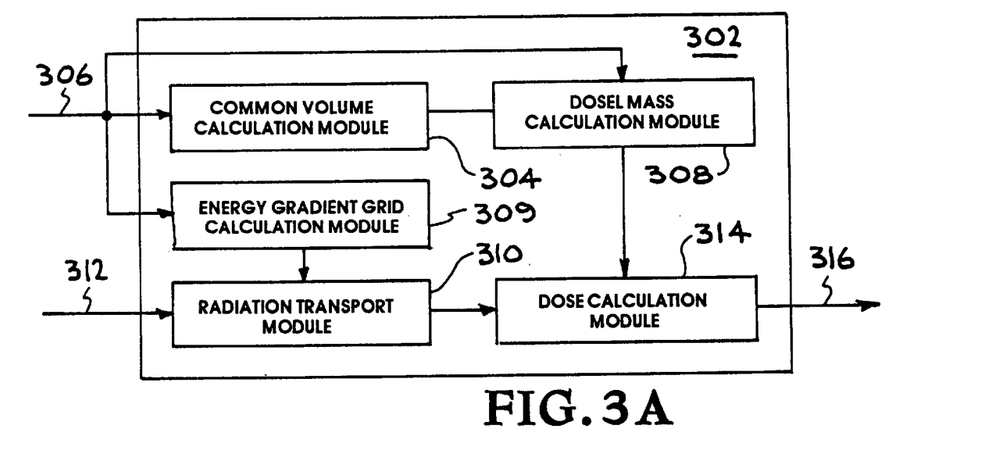
FIG. 3A is a block diagram of a computer system for effecting the present invention.

FIG. 3A is a block diagram of a computer 302 for effecting the present invention. The computer 302 contains a set of software modules which implement various steps in the present invention. The computer 302 can be an ordinary, single processor personal computer, however those skilled in the art will know that the present invention may be embodied within more powerful machines. The computer 302 includes an internal memory for storing computer program instructions which control how a processing unit within the computer accepts, transforms, and outputs data. The internal memory includes both a volatile and a non-volatile portion. Those skilled in the art will recognize that the internal memory can be supplemented with computer memory media, such as such as a compact disk, flash memory cards, a magnetic disc drive or a dynamic random access memory.

Before the computer 302 can calculate an amount of radiation deposited by the particle transport beam 112, a user must specify a resolution and set of physical dimensions for the dosel grid 108. Higher-resolution calculations take longer to reach a specified statistical uncertainty, but will give more detailed information about a spatial distribution of the dose. Lower-resolution calculations will reach an equivalent statistical uncertainty sooner.

A common volume calculation module 304, within the computer 302, accepts the input parameters 200 on line 306 and calculates a set of common volumes between a single dosel, within the set of dosels 110, and a subset of the voxels 106, which overlap the single dosel. Since the dosel grid 108 typically includes a large number of dosels 110 and the voxel grid 104 also tends to have a large number of voxels 106, calculating the set of common volumes has a potential for requiring a significant amount of computer time.

To further enhance calculation speed, the present invention discloses a closed-form solution for calculating a common volume between a spherical dosel and a rectangular parallelepiped voxel. An expression for the closed-form solution for calculating a common volume between a sphere and a rectangular parallelepiped is first presented, followed by a derivation.

Consider a sphere of radius (r).

Define an (x, y, z) coordinate system with an origin at a center of the sphere. Normalize x, y, and z in terms of the radius of the sphere (i.e. divide x, y, and z by r).

Consider a voxel which overlaps the sphere but which is located in only one octant of the sphere. [Note: The voxels must be sliced into sub-voxels, such that each sub-voxel is located in only one octant of the sphere.]

Say that the voxel is located in an octant of the sphere where x, y, and z are all positive. [Extension of the closed form solution to other octants is similar.]

Define a "corner volume," $V3(x, y, z)$, associated with a point (x, y, z) to be a volume bounded by an xy plane that goes through (x, y, z)

an xz plane that goes through (x, y, z)

a yz plane that goes through (x, y, z)

a surface of the sphere.

Of the eight volumes fitting this description, choose the volume that falls entirely within the octant of the sphere in which (x, y, z) is located.

Say that a corner of the voxel that is located closest to an origin is at (x0, y0, z0) and that a width for each side of the voxel is dx, dy, dz respectively. Since x, y, and z have been normalized in terms of r, the width of the voxel is dx*r.

Then, by inspection, the closed form solution to the common volume between the voxel and the sphere is:

$$V = V3(x0, y0, z0) - \begin{bmatrix} V3(x0 + dx, y0, z0) + \\ V3(x0, y0 + dy, z0) + \\ V3(x0, y0, z0 + dz) \end{bmatrix} + \quad (1)$$

$$\begin{bmatrix} V3(x0 + dx, y0 + dy, z0) + \\ V3(x0 + dx, y0, z0 + dz) + \\ V3(x0, y0 + dy, z0 + dz) \end{bmatrix} -$$

$$V3(x0 + dx, y0 + dy, z0 + dz)$$

A first term in this formula is the common volume of the sphere and the voxel plus some other volumes. Later terms in the formula subtract out those other volumes.

A derivation of the closed form solution now follows:

It will be shown that:

$$V3(x, y, z) = \frac{r^3}{6} \left\{ \begin{array}{l} g(x, y, z) + \\ f(x, y) + f(x, z) + f(y, z) \end{array} \right\} \quad (2)$$

where:

$$g(x,y,z) = -2\pi - 6xyz$$

$$g(x, y, z) = -2\pi - 6xyz + \frac{\pi}{2}\{x(3-x^2) + y(3-y^2) + z(3-z^2)\} \quad (3)$$

and:

$$f(x, y) = 2xy\sqrt{1-x^2-y^2} + 2\text{ArcTan}\left(\frac{\sqrt{1-x^2-y^2}}{xy}\right) - \quad (4)$$

$$x(3-x^2)\text{ArcTan}\left(\frac{\sqrt{1-x^2-y^2}}{y}\right) -$$

$$y(3-y^2)\text{ArcTan}\left(\frac{\sqrt{1-x^2-y^2}}{x}\right)$$

Equation 2 is derived as follows:

Let:

$$V2(x,y) = V3(x,y, 0) \quad (5)$$

V2(x, y) is one half a volume bounded by:
- an xz plane through (x, y,0)
- a yz plane through (x, y,0)
- a surface of the sphere.

Of the four such volumes, choose the volume lying in the quadrant containing (x, y).

Spherical symmetry implies that V3(x, y, z) and V2(x, y) are invariant under permutation of their arguments. It will be shown that V3(x, y, z) can be written in terms of V2(x, y), V2(y, z), etc. An expression for V2(x, y) can then be derived.

Draw an xy, xz, and a yz plane through the point (x, y, z). These planes divide the octant of the sphere containing the point (x, y, z) into eight sub-octants. Let $V_{+-+}$ denote a volume of the sub-octant that is located along +x, −y, +z directions. V2(x, y) is a part of the octant that has values of x and y more positive than the point (x, y, z). V2(x,0) is a part of the octant that has values of x more positive than the point (x, y, z).

By inspection:

$$V2(x, y) = V_{+++} + V_{++-} \quad (6)$$

$$V2(x, z) = V_{+++} + V_{+-+}$$

$$V2(y, z) = V_{+++} + V_{-++}$$

$$V2(x, 0) = V_{+++} + V_{++-} + V_{+-+} + V_{+--}$$

$$V2(y, 0) = V_{+++} + V_{++-} + V_{-++} + V_{-+-}$$

$$V2(z, 0) = V_{+++} + V_{+-+} + V_{-++} + V_{--+}$$

Combining the above expressions gives:

$$V2(x, 0) + V2(y, 0) + V2(z, 0) - [V2(x, y) + V2(x, z) + V2(y, z)] = \quad (7)$$

$$V_{octant} - V_{+++} - V_{---}$$

$$\text{where: } V_{octant} = \frac{\pi r^3}{6}$$

where, $V_{octant}$ is a total volume of the octant of the sphere.

Equation 7 follows from the fact that its left hand side contains every sub-octant other than $V_{+++}$ and $V_{---}$. But $V_{+++} = V3(x, y, z)$ and $V_{---} = r^3 xyz$.

Thus, rewriting Equation 7 gives:

$$V3(x, y, z) = \frac{\pi r^3}{6} - xyzr^3 - \quad (8)$$

$$[V2(x, 0) + V2(y, 0) + V2(z, 0)] +$$

$$V2(x, y) + V2(x, z) + V2(y, z)$$

In order to complete derivation of Equation 2, an integral must be taken to obtain an expression for V2(x, y). Begin by calculating a volume on a unit sphere and then multiply the result by $r^3$.

Figure 4:
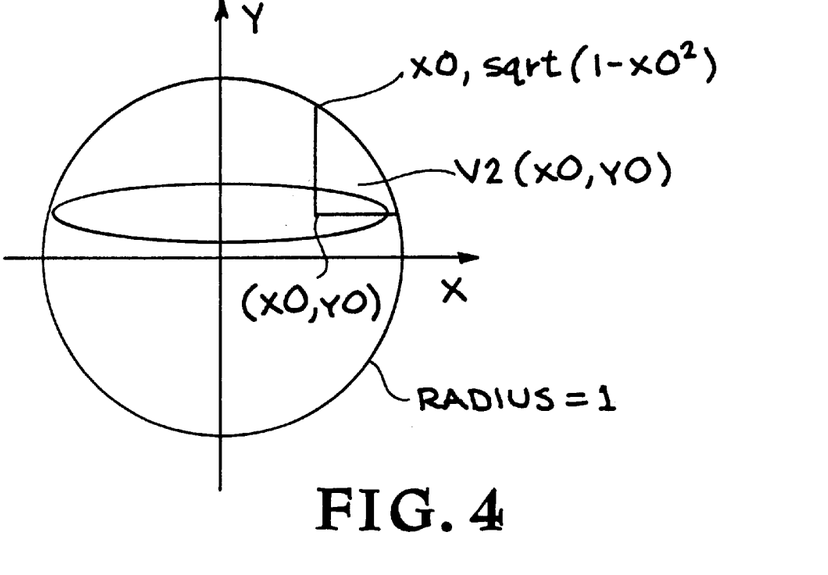
FIG. 4 is a graph of a three-dimensional sphere.
Figure 5:
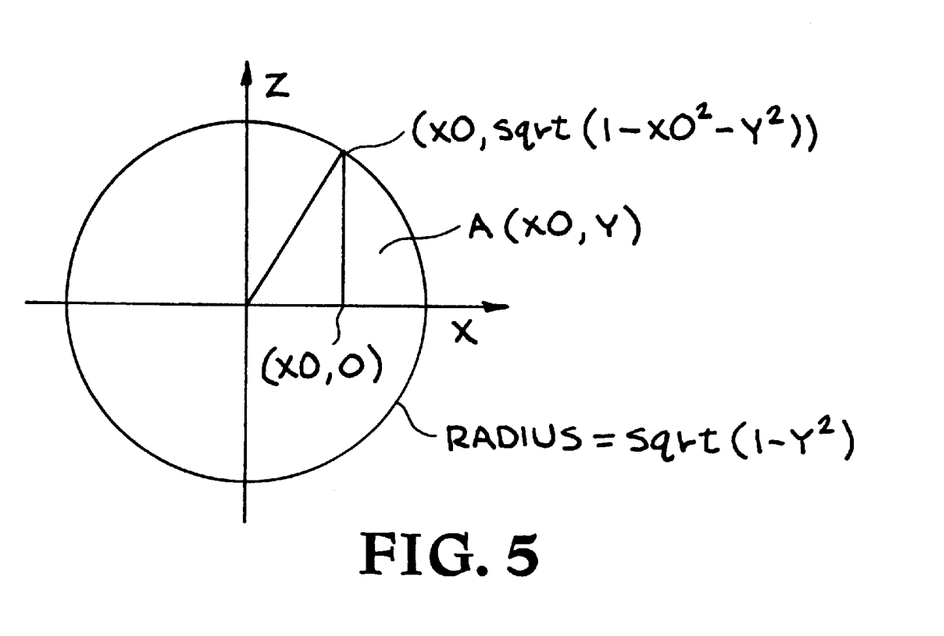
FIG. 5 is a graph of a two-dimensional slice of the three-dimensional sphere of FIG. 4 at an arbitrary value of y.

Consider FIGS. 4 and 5. FIG. 4 is a graph of a three-dimensional sphere. FIG. 5 is a graph of a two-dimensional slice of the three-dimensional sphere of FIG. 4 at an arbitrary value of y.

From FIGS. 4 and 5:

$$V2(x0, y0) = r^3 \int_{y0}^{\sqrt{1-x0^2}} A(x0, y) dy$$

where:

$$A(x0, y) = \frac{1}{2}\left[(1-y^2)\text{ArcCos}\left(\frac{x0}{\sqrt{1-y^2}}\right) - x0\sqrt{1-x0^2-y^2}\right] \quad (9)$$

One can read a formula for A(x0, y) off of the second drawing since it is just the area of the pie cut minus the area of the triangle.

Next, change the variable of integration from y to t where:

$$\text{Cos}(t) = \frac{x0}{\sqrt{1-y^2}}$$

This gives:

$$V2(x0, y0) = \frac{r^3 x0^4}{2} \tag{10}$$

$$\int_0^{\text{ArcCos}\left(\frac{x0}{\sqrt{1-y0^2}}\right)} \frac{1}{\sqrt{\cos^2(t) - x0^2}} \frac{\sin(t)}{\cos^3(t)} \left(\frac{t}{\cos(t)} - \sin(t)\right) dt$$

Find the indefinite integral, h(x0, t), of Equation 10 using "Mathematica" software (designed by Wolfram Research of Champagne-Urbana, Ill.).
Simplification of the result gives:

$$h(x0, t) = \tag{11}$$

$$\frac{r^3}{6} \begin{bmatrix} x0(-3 + x0^2)\text{ArcTan}\left(\frac{x0 \sin(t)}{\sqrt{\cos^2(t) - x0^2}}\right) + \\ 2\text{ArcTan}\left(\frac{\sin(t)}{\sqrt{\cos^2(t) - x0^2}}\right) - \\ \frac{\sqrt{\cos^2(t) - x0^2}}{\cos(t)} \left\{2t + x0^2\left[\frac{t}{\cos^2(t)} - 2\tan(t)\right]\right\} - \\ 2\sqrt{-1} \ln\left(\sqrt{2(1-x0^2)}\right) \end{bmatrix}$$

Mathematica includes an imaginary constant of integration. Taking the derivative of Equation 11 confirms that it is the integral of Equation 10.

Putting in limits of integration from Equation 10 and simplifying results in:

$$V2(x, y) = \frac{r^3}{6} \begin{bmatrix} 2xy\sqrt{1 - x^2 - y^2} + \\ 2\text{ArcTan}\left(\frac{\sqrt{1-x^2-y^2}}{xy}\right) - \\ x(3-x^2)\text{ArcTan}\left(\frac{\sqrt{1-x^2-y^2}}{y}\right) - \\ y(3-y^2)\text{ArcTan}\left(\frac{\sqrt{1-x^2-y^2}}{x}\right) \end{bmatrix} \tag{12}$$

This implies that:

$$V2(x, 0) = \frac{r^3 \pi}{6} \left\{1 - \frac{x(3-x^2)}{2}\right\} \tag{13}$$

Then substituting Equations 12 and 13 into Equation 8 results in Equation 2.

Common volume calculation speed can be further increased by shrinking the unit cells 113 (i.e. the dosel grid spacing) and increasing a total number of dosels so as to cover a same dosel grid volume. When a larger number of dosels span the voxel grid 104, a pattern of dosels and voxels repeats periodically within the dosel grid 108. As a result of this periodicity, only a first set of common volumes between one period of dosels and voxels need be calculated. This first set of common volumes can then be re-used for all subsequent sets of common volumes, due to this periodicity.

Dosel grid spacing is preferably shrunk so that, $$m\text{Dx}_v = n\text{Dx}_d \tag{14}$$

where:
  n and m are integers;
  $\text{Dx}_d$ is the spacing of the dosel grid 108;
  $\text{Dx}_v$ is the spacing of the voxel grid 104 in x or y, where x and y are grid axes of a single CT or MRI slice. The coordinate, x or y, used in Equation 14 is the one which has a larger number of voxel grid points in the region spanned by the dosel grid 108, labeled a "long direction." Voxel grid points are defined at each corner of the voxels 106;
  m, n, and $\text{Dx}_d$ are chosen such that (n $\text{Dx}_d$) is about 1/q of the way across the dosel grid in the long direction. A reasonable trade-off between quickly calculating the set common volumes and small fractional changes in the unit cell 113 is obtained by setting "q" equal to five.

When equation 14 is true, the voxel grid 104 and the dosel grid 108 are co-synchronous. Under co-synchronous conditions, the common volumes of the voxels 106 and the dosels 110 are calculated only for a first n dosels, since the common volumes are periodic with period n in the dosel grid 108 and with period m in the voxel grid 104. Furthermore, when $\text{Dx}_v = \text{Dy}_v$, the voxel grid 104 and the dosel grid 108 are co-synchronous in both x and y directions, and so the common volumes of the voxels 106 and the dosels 110 need only be calculated for the first n dosels along both axis. This speeds up calculations by as much as a factor of 20 for q=5. When $\text{Dx}_v$ is not equal to $\text{Dy}_v$, the co-synchronous nature of the voxel grid 104 and the dosel grid 108 exists only in the long direction. If $\text{Dx}_d$ has changed by more than 20%, an original value of $\text{Dx}_d$ entered by a user is saved and the common volumes for all of the dosels 110 are calculated.

Using the closed form solution and once the dosel grid spacing has been shrunk, the common volume calculation module 304 calculates V3(x, y, z) for every grid point of the voxel grid 104 that is located inside each of the dosels. Portions of the voxels 106 that lie in more than one octant of a dosel must be treated as separate voxels in order to use Equation 2. This amounts to calculating V3 for the following sets of points that are not on the voxel grid 104:

an intersection of an edge the voxels with planes x=0, y=0, and z=0. (x, y, z)=(0,0,0) is at the center of the dosel;
  an intersection of a plane of the voxels with the x, y, and z axes; and
  a center of the dosel.

If these new points are identical with points in the voxel grid 104, V3 is calculated for both sets of points. These extra points give rise to zero volume voxels which does not effect the common volume calculation, but does result in some unnecessary computation. The common volume calculation module 304 then, uses the values of V3 to calculate the common volume of the dosel and every voxel which the dosel overlaps, using Equation 1.

Using the set of common volumes calculated by the common volume calculation module 304, a dosel mass module 308, within the computer 302, multiplies a common volume, from within the set of common volumes by a mass density of each of the voxels 106, overlapping the common volume, to obtain an incremental dosel mass. The dosel mass module 308 receives the mass density of each of the voxels 106 from the input parameters 306. Incremental dosel masses are calculated for each common volume within the set of common volumes. Next, the dosel mass module 308 adds up all of the incremental dosel masses to obtain the dosel mass for a dosel. Dosel masses are calculated for each dosel in the set of dosels 110.

An energy gradient grid calculation module 309 calculates an energy gradient grid in preparation for charged particle tracking, discussed infra. The energy gradient grid consists of a set of energy values representing an energy required for a charged particle, located outside of the dosel grid 108, to reach and enter one of the dosels 110. Charged particles close to a dosel require less energy to enter the dosel than charged particles further away from the dosel. As a result, the energy values calculated by the energy gradient grid calculation module 309 form a gradient. An energy value is calculated for each voxel that does not entirely fall within the dosel grid 108.

More specifically, within the present invention charged particles are no longer tracked once their remaining Continuous Slowing Down Approximation (CSDA) range of travel, as determined by their kinetic energy, T, gets small enough that their energy deposition is known. This is done to increase calculation speed. The energy gradient grid calculation module 309 assigns each voxel a minimum tracking energy, $T_{min}$. Later, during each step of a charged particle transport calculation, discussed infra., the T of a charged particle is compared to a value of $T_{min}$ that goes with a voxel containing the charged particle. When T falls below this value, the charged particle is no longer tracked and its energy is deemed to be deposited within the target mass or as given to a daughter particle, which is then tracked independently.

To generate a value for $T_{min}$, first, the voxel grid, having a right parallelepiped shape, is defined. Voxels within the voxel grid are also right parallelepipeds. Density and material identity are constant inside the voxels. Radiation transport is calculated throughout the voxel grid, however, a dose is saved only in the dosel grid. Procedures for calculating $T_{min}$ are different depending upon whether a charged particle is inside or outside of the dosel grid.

Inside the dosel grid, each voxel is assigned a $T_{min}$ such that a corresponding CSDA range is 0.3 times a minimum dimension of the voxel. A first shell of voxels lying completely outside the dosel grid are also assigned $T_{min}$ in this fashion. Note that $T_{min}$ is much smaller for air voxels than for water voxels. A spatial error in a dose that arises from stopping charged particle tracking at this energy should be small compared to a spatial resolution of knowledge about the target mass.

Outside the dosel grid, since $T_{min}$ is a minimum kinetic energy, over all possible paths, required for a charged particle to reach a voxel in the first shell outside of the dosel grid, a charged particle with $T<T_{min}$ will not reach the dosel grid. A change of T with distance traveled is obtained using the CSDA approximation.

Figure 3B:
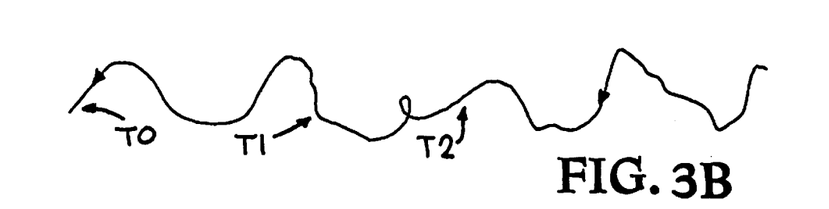
FIG. 3B is a pictorial diagram of a charged particle that follows a known path.

Solving for $T_{min}$ involves recognizing that a smallest energy loss path may take a shortest geometrical path to a low density region and then follow low densities along a curved path into the dosel grid. The value of $T_{min}$ is not affected by any estimate of the fraction of the charged particles that will actually follow the path all the way into the dosel grid. $T_{min}$ is calculated by first considering a simpler problem of finding a value of T for the charged particle that follows a known path so as to end a path with kinetic energy $T_o$. Tracing backwards along the path, see FIG. 3B, say that the charged particle:

enters material #1, with kinetic energy $T_1$ and leaves with $T_0$ after having traveled a distance along the curved path of $Dx_1$.

enters material #2, with kinetic energy $T_2$ and leaves with $T_1$ after having traveled a distance along the curved path of $Dx_2$.

etc.

Let:

$$S_m(T) = \frac{1}{\rho}\frac{dT}{dx} = \text{mass stopping power of material } \# m \text{ at } T \quad (1)$$

$\rho_m$ = density of material # m $$R_m(T) = \int_0^T dT' \frac{1}{S_m(T')}$$

$= CSDA$ range of material # m at $T$

Then, one can solve for T1, T2, T3, . . . by sequentially solving the equations:

$R_1(T_1) = \rho_1 \Delta x_1 + R_1(T_0)$ $R_2(T_2) = \rho_2 \Delta x_2 + R_2(T_1)$ $R_3(T_3) = \rho_3 \Delta x_3 + R_3(T_2)$ etc. $\quad (2)$ This involves solving an equation at every material boundary. A computationally faster procedure may be developed as follows. Let $S_u(T)$ be a minimum stopping power at each T of all the materials in the voxel grid.

$$S_u(T) = \text{Min}(S_1(T), S_2(T), S_3(T), \ldots) \quad (3)$$

Define $R_u(T)$ to be the corresponding CSDA range as defined in Equation 1. Replace a stopping power of every voxel in the voxel grid with $S_u(T)$. Then Equation 2 goes to:

$R_u(T_1) = \rho_1 \Delta x_1 + R_u(T_0)$ $R_u(T_2) = \rho_2 \Delta x_2 + R_u(T_1)$ $R_u(T_3) = \rho_3 \Delta x_3 + R_u(T_2)$ etc. $\quad (4)$ which is equivalent to:

$$R_u(T_i) = R_u(T_0) + \rho_1 \Delta x_1 + \ldots + \rho_i \Delta x_i \quad (5)$$

Let $T_i$ be a solution of Equations 2 and $T_i'$ be the corresponding solution of Equation 5. One can show that $T_i' <= T_i$. Therefore, using Equation 5 in place of Equations 2 speeds up a setup calculation for $T_{min}$, even though charged particles are tracked to lower energies than necessary.

Now consider the problem of finding a path from a given point outside the dosel grid down to the first shell of voxels outside the dosel grid which minimizes T according to Equation 5 with $T_0 = T_{min}$ of a voxel in the first shell. Since $R_u(T)$ is a monotonically increasing function of T, this is equivalent to minimizing a path length, P, given by:

$$P = R_u(T_0) + \rho_1 \Delta x_1 + \rho_2 \Delta x_2 + \ldots + \rho_n \Delta x_n \quad (6)$$

Here "n" denotes the voxel in which $T_{min}$ is being calculated.

Some approximations are made to get a tractable problem:

1) P is calculated at a center point of each voxel.
2) Only paths that go between center points in directions parallel to the x, y, and z axes are considered.

These approximations are compensated by:

1) Subtracting one half of a voxel length, along an axis by which the short path entered the voxel, from P. This sets $T_{min}$ of the voxel by an edge of the voxel that is closest to the dosel grid.
2) Multiplying $P_{min}$ by 1/sqrt(3). This compensates for diagonal paths that are not allowed.

The short path is found by growing the solution outwards from the dosel grid through successive shells of voxels that surround the dosel grid. As already stated, in the first shell of voxels, $T_0$ in Equation 6 is assigned such that the corresponding CSDA range is 0.3 times a minimum dimension of the voxel. In the second shell of voxels, an initial value for $P_{min}$ is assigned by growing the paths straight outwards from the first shell of voxels. The program then sweeps inside the second shell of voxels looking for shorter paths.

Figures 3C, 3D:
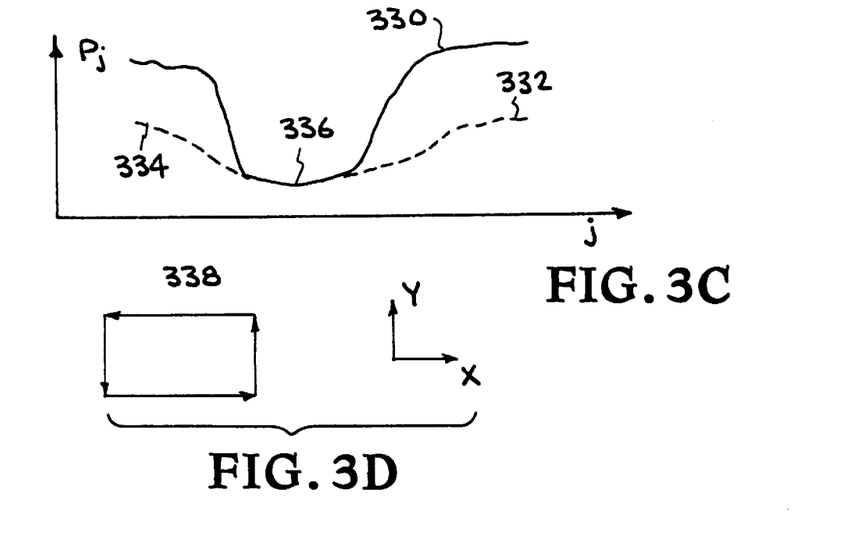
FIG. 3C is a graph of a one dimensional sweeping method.
FIG. 3D is a pictorial diagram of a path for scanning a second shell of voxels.

The sweeping method is easiest to explain in one dimension, see FIG. 3C. Say that j is a voxel index along a line in the second shell of voxels and that a solid line 330 for $P_j$ is a path length obtained from Equation 6 by growing a path straight out from the first shell of voxels. Now sweep in a direction of increasing j while saying that:

$$P_{j+1} = \text{Min}\left(P_{j+1}, P_j + \frac{\rho_j + \rho_{j+1}}{2}\Delta x\right) \quad (7)$$

where Dx is a width of the voxels. This will generate dotted line 332 on the right. A charged particle in one of the voxels in this dotted line has a shorter path by traveling left in the second shell of voxels and then going down to the first shell of voxels instead of going straight down to the first shell of voxels. The dotted line 324 on the left is generated by sweeping in a direction of decreasing j and saying that:

$$P_{j-1} = \text{Min}\left(P_{j-1}, P_j + \frac{\rho_j + \rho_{j-1}}{2}\Delta x\right) \quad (8)$$

Thus, the short path solution is grown out from low points 336 by sweeping along and determining if a voxel that is ahead of a current voxel can decrease its path by connecting to the current voxel.

One can grow out from a two dimensional low spot by doing a raster scan in +x and +y while looking ahead in +x and +y directions. This will grow the low spot out in the (+x, +y) quadrant. In order to grow the low spot out in all directions, one must do raster scans in four directions; namely (+x, +y), (+x, −y), (−x, +y), and (−x, −y).

A general method for growing the short path solution is thus presented. A set of steps for implementing the short path solution is:

1) calculate $T_{min}$ for a dosel grid and a first shell of voxels outside the dosel grid such that a corresponding CSDA range is 0.3 times a minimum dimension of a voxel within the first shell of voxels;
2) grow paths straight out from each voxel in the first shell of voxels to an adjacent voxel in a second shell of voxels, which may be missing some surfaces;
3) raster scan the second shell of voxels such that low points can grow around corners of the second shell of voxels by performing the steps of:
   A) selecting a lowest value of z in a z-plane;
   B) scan the second shell of voxels along a path 338, see FIG. 3D;
   C) go around the path 338 twice;
   D) while scanning along path 338 test whether a first voxel that lies ahead in the x or y directions, and whether a second voxel that lies above in the z direction, can decrease a path length by connecting to a current voxel.
   E) step up to a next higher value of z; and
   F) repeat steps A through E for all values of z;
4) The scan in step 3 is analogous to moving in a positive z direction along threads of a right handed screw while testing voxels that lie ahead in directions of travel along the threads of the screw and down an axis of the screw. Next do the following scans, while always testing ahead in directions of motion:
   A) Move in a negative z direction along a right handed screw.
   B) Move in positive and negative z directions along a left handed screw.
   C) Do analogous scans for screws lying along the x axis and the y axis. This completes scans for the second shell of voxels.
5) repeat steps 2 through 4 to generate path lengths for each additional shell of voxels; and
6) after completing an outermost shell of voxels, move back through the shells towards the dosel region while repeating steps 3 and 4. In these inward moving scans, test ahead in all three directions of motion (two directions in a current shell and an inward direction perpendicular to the current shell).

This completes the energy gradient grid calculation.

Next, a radiation transport module 310, within the computer 302, receives dosel and voxel position, spacing, and common volume information from the common volume calculation module 304. The radiation transport module 310 receives the energy gradient grid from the energy gradient grid calculation module 309. The radiation transport module 310 receives particle transport beam data on line 312. The particle transport beam data include the following information on particles within the particle transport beam 112: location, energy, statistical weight, particle type, direction, and a distribution representing probabilities that particles generated by a source will reach and interact with the target. Since, in the present invention, the dosel grid 108 is de-coupled from the voxel grid 104, the radiation transport module 310 tracks only those particles within or likely to enter the dosel grid 108. Thus, computational power is not allocated toward tracking particles not within and not likely to enter the dosel grid 108.

Uncharged particles, such as photons and neutrons, and charged particles, such as electrons, positrons, protons, alpha particles, are tracked by the radiation transport module 310 using different routines.

The uncharged particles are tracked by the radiation transport module 310 interaction-by-interaction and explicit (x, y, z) coordinates are identified for each energy deposition associated with each interaction. All primary uncharged particles (i.e. those part of the particle transport beam 112) are tracked until they either interact with the target mass in or leave the voxel grid 104. However, secondary uncharged particles (i.e. those resulting from a collision of the particle transport beam 112 with the target mass and sometimes called daughter particles), are subjected to variance reduction techniques.

If a secondary uncharged particle is formed within the dosel grid 108, the secondary uncharged particle is tracked as described for the primary uncharged particles. If a secondary uncharged particle is formed outside of the dosel grid 108 and the secondary uncharged particle is heading toward the dosel grid 108, the secondary uncharged particle is tracked as described for the primary uncharged particles.

However, if a secondary uncharged particle is formed outside of the dosel grid 108 and the secondary uncharged particle is heading away from the dosel grid 108, well known variance reduction techniques, such as Russian Rouletting and particle splitting are applied to the secondary uncharged particle. Russian Rouletting and particle splitting techniques are discussed on page 16 of "Particle-Transport Simulation with the Monte Carlo Method" by L. L. Carter and E. D. Cashwell, ERDA Critical Review Series, 1975, and on page 58 of "Monte Carlo Particle Transport Methods: Neutron and Photon Calculations", by Ivan Lux and Laszlo Koblinger, CRC Press, Boca Raton, 1991.

If the secondary uncharged particle survives the Russian Rouletting, the secondary uncharged particle is tracked as described for the primary uncharged particles. However, particle splitting techniques are employed to reduce statistical fluctuations should the secondary uncharged particle re-enter the dosel grid 108.

The radiation transport module 310 tracks all charged particles passing through the dosel grid 108. For charged particles outside of the dosel grid 108, the radiation transport module 310 employs the variance reduction technique of range rejection. Range rejection is a technique which does not track (i.e. rejects) particles which do not have an energy (i.e. a range) capable of transporting the charged particle into the dosel grid 108. Range rejection techniques are more fully described in a reference entitled "Monte Carlo Transport of Electrons and Photons," by Jenkins et al., Plenum Press, New York, 1988.

To begin range rejection, the radiation transport module 310 calculates an energy value (E0) associated with a charged particle, using the particle beam transport data received on line 312. The radiation transport module 310 then accesses the energy gradient grid, created earlier by the energy gradient grid calculation module 309, and retrieves an energy value (E1) required of the charged particle to enter the dosel grid 108. If E0 less than E1, the charged particle does not have enough energy to enter the dosel grid 108 and so the radiation transport module 310 discontinues tracking the charged particle. If E0 is greater than or equal to E1, the radiation transport module 310 keeps tracking the charged particle. Using the energy gradient grid along with range rejection techniques is herein defined as gradient charged-particle tracking.

For those charged particles which are tracked, the radiation transport module 310 models the charged particles as if they deposit energy both continuously and through discrete interactions. Using this model, the radiation transport module 310 first tracks a path a charged particle takes while passing through the voxel grid 104. The charged particle deposits a predetermined energy over the path. Next, the radiation transport module 310 assigns an energy value to several random (x, y, z) points along the path. A sum of the assigned energy values at random points over the path of the charged particle is equal to the predetermined energy. Some of the random points may lie within the dosel grid 108 and some may not. In contrast, when the charged particle deposits energy in a discrete interaction at a particular location (x, y, z), the radiation transport module 310 assigns the deposited energy to that particular location.

Output from the radiation transport module 310 consists of a large number of energy depositions at various point locations (x, y, z). This is in contrast to typical Monte Carlo radiation transport codes which only generate one energy deposition value per voxel.

A dose calculation module 314, within the computer 302, receives dosel masses for each of the dosels 110 from the dosel mass module 308, and a set of energy depositions at various (x, y, z) locations from the radiation transport module 310. To begin, the dose calculation module 314 identifies a location (x, y, z) for an energy deposition. Next, the dose calculation module 314 identifies which of the overlapping dosels 110, if any, contain the location (x, y, z). The energy deposition associated with the location (x, y, z) is then divided by the mass of each dosel containing (x, y, z) to obtain an incremental dose for each of those dosels. The dose calculation module 314 performs these steps for each of the energy depositions, resulting in a total dose for each dosel. The dose calculation module 312 then outputs a set of doses for each of the dosels 110, on line 316.

Figure 6:
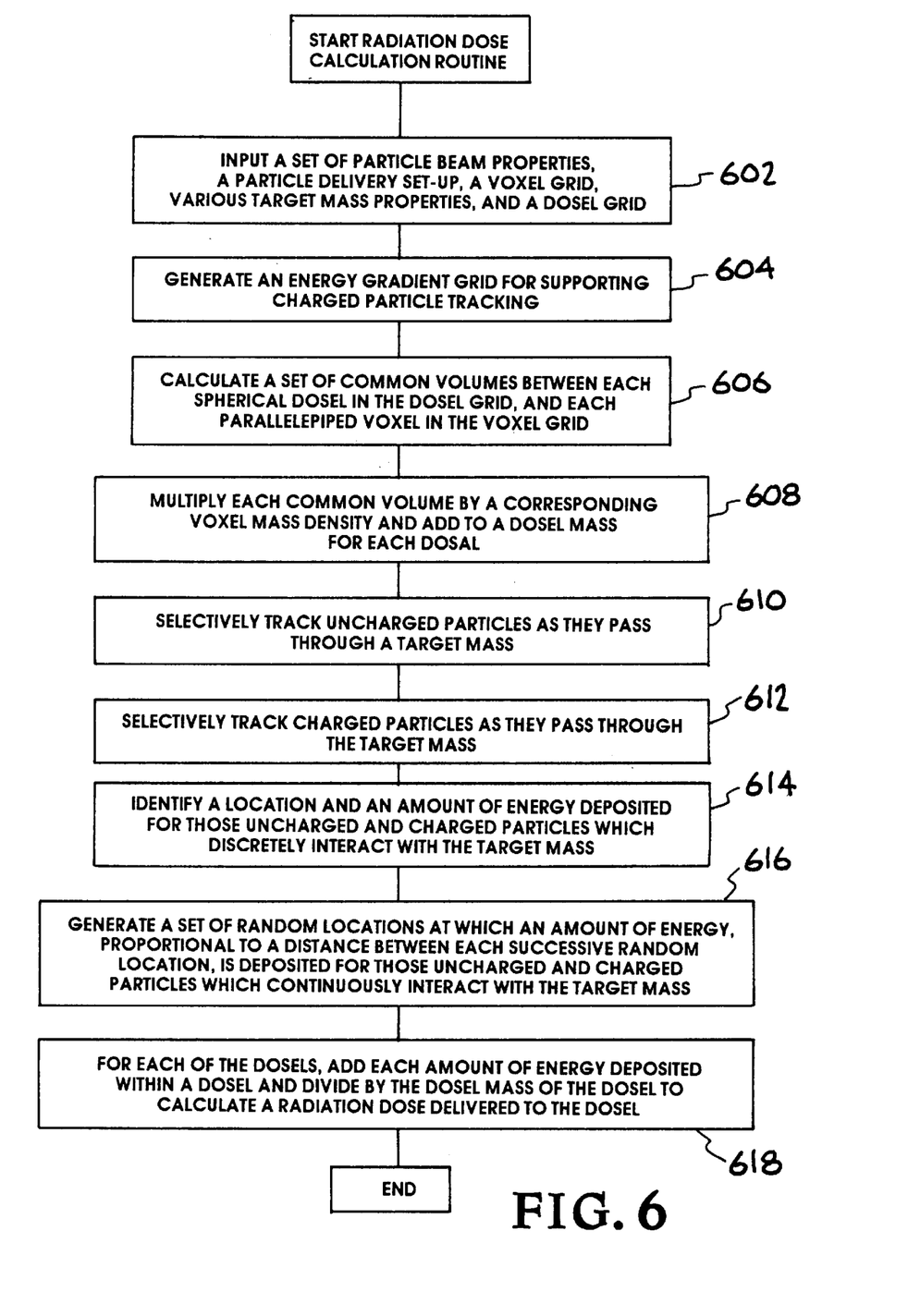
FIG. 6 is a flowchart of a method for radiation dose calculation within sub-volumes of a Monte Carlo based particle transport grid.

FIG. 6 is a flowchart of a method for radiation dose calculation within sub-volumes of a Monte Carlo based particle transport grid. The method begins in step 602 where the common volume calculation module 304 and the energy gradient grid calculation module 309 receive as input a set of particle beam properties, a particle delivery set-up, a voxel grid, various target substance properties, and a dosel grid. In step 604, the energy gradient grid calculation module 309 generates an energy gradient grid for supporting charged particle tracking. Step 604 is expanded upon in FIG. 7. Next, in step 606, the common volume calculation module 304 calculates a set of common volumes between each spherical dosel in the dosel grid 108, and each parallelepiped voxel in the voxel grid 104. The dosel mass module 308 multiplies each common volume by a corresponding voxel mass density to create an incremental dosel mass, which is then added to a total dosel mass of a corresponding dosel, in step 608. Next, in step 610, the radiation transport module 310 selectively tracks uncharged particles as they pass through a target mass. Step 610 is expanded upon in FIG. 8. In step 612, the radiation transport module 310 selectively tracks charged particles as they pass through the target mass. Step 612 is expanded upon in FIG. 9. The radiation transport module 310 identifies a location and an amount of energy deposited for those uncharged and charged particles which discretely interact with the target mass, in step 614, as described earlier. In step 616, the radiation transport module 310 generates a set of random locations at which an amount of energy, proportional to a distance between each successive random location, is deposited for those charged particles which continuously interact with the target mass, also as earlier discussed. Next, in step 618, the dose calculation module 314, for each of the dosels, adds each amount of energy deposited within a dosel and divides by the dosel mass of the dosel to calculate a radiation dose delivered to the dosel. After step 618, the process of radiation dose calculation is complete.

Figure 7:
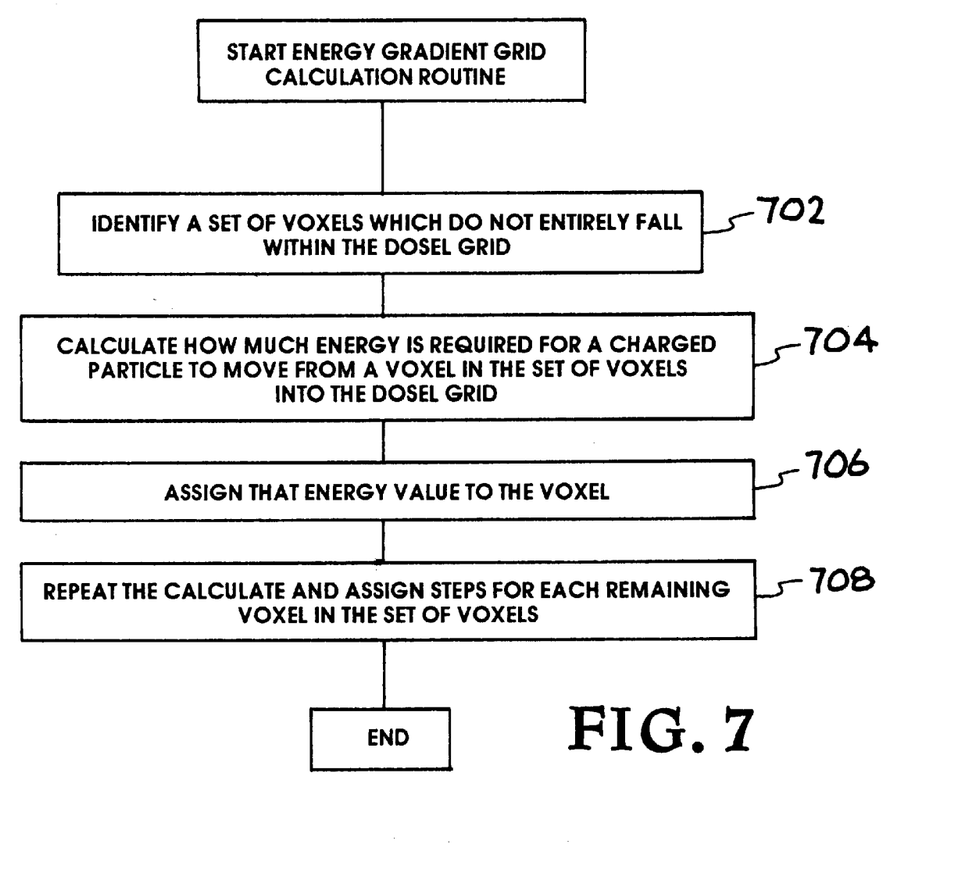
FIG. 7 is a flowchart of a method for energy gradient grid calculation.

FIG. 7 is a flowchart of a method for energy gradient grid calculation (step 604 of FIG. 6). The method begins in step 702 where the energy gradient grid calculation module 309 identifies a set of voxels which do not entirely fall within the dosel grid 108. Next, in step 704, the energy gradient grid calculation module 309 calculates how much energy is required for a charged particle to move from a voxel in the set of voxels into the dosel grid. The energy gradient grid calculation module 309 assigns that energy value to the voxel, in step 706. Next, in step 708, the energy gradient grid calculation module 309 repeats the calculate and assign steps for each remaining voxel in the set of voxels. After step 708, the process of energy gradient grid calculation is complete.

Figure 8:
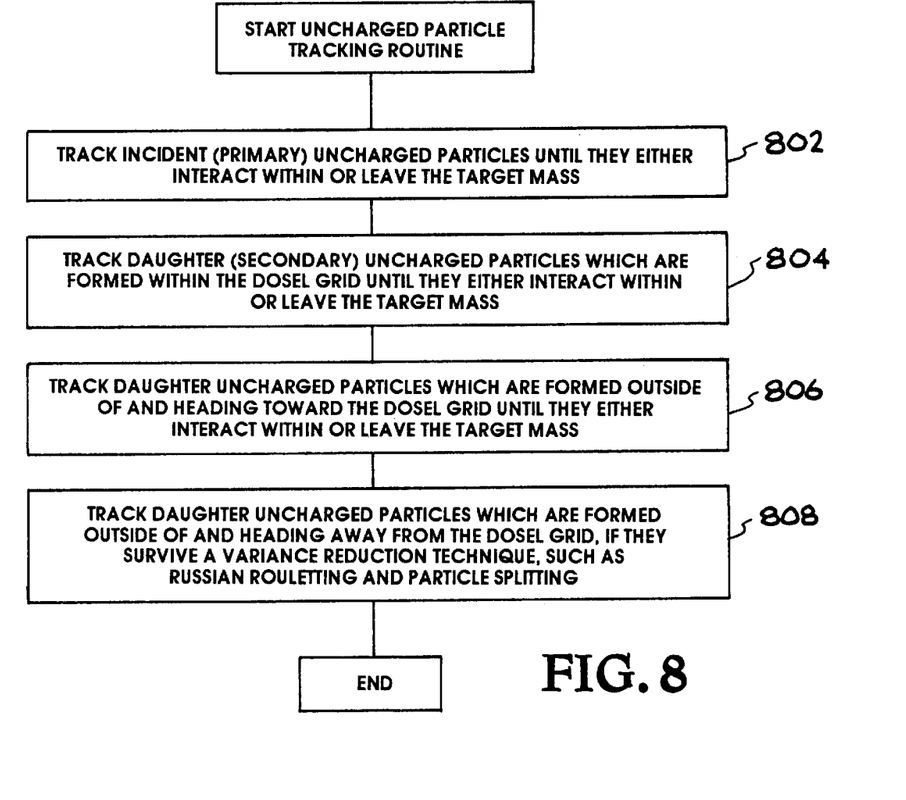
FIG. 8 is a flowchart of a method for uncharged particle tracking.

FIG. 8 is a flowchart of a method for uncharged particle tracking (step 610 of FIG. 6). The method begins in step 802 where the radiation transport module 310 tracks incident (a.k.a. primary) uncharged particles until they either interact within or leave the target mass. Next, in step 804, the radiation transport module 310 tracks daughter (secondary) uncharged particles which are formed within the dosel grid 108 until they either interact within or leave the target mass. The radiation transport module 310 tracks daughter uncharged particles which are formed outside of and heading toward the dosel grid 108 until they either interact within or leave the target mass, in step 806. Next, in step 808, the radiation transport module 310 tracks daughter uncharged particles which are formed outside of and heading away from the dosel grid, if they survive a variance reduction technique, such as Russian Rouletting and particle splitting. After step 808, the process of uncharged particle tracking is complete.

Figure 9:
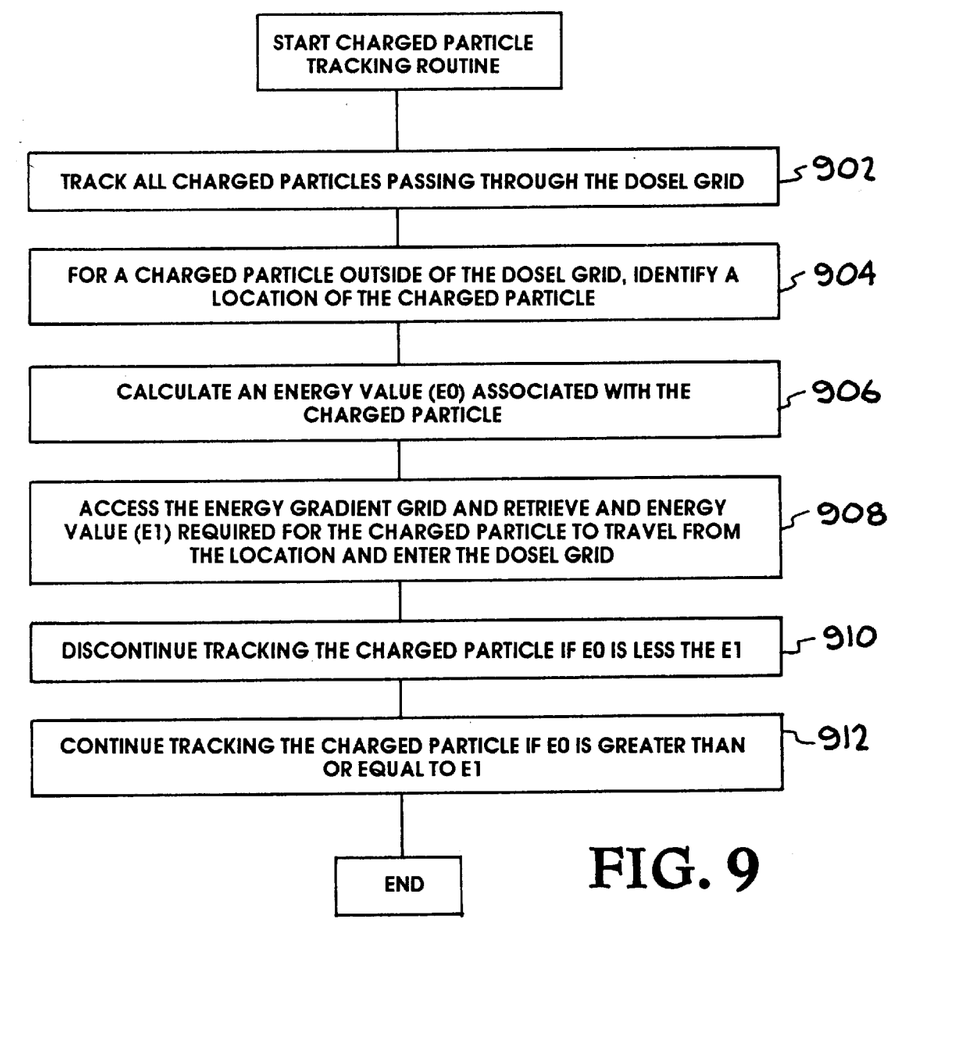
FIG. 9 is a flowchart of a method for charged particle tracking.

FIG. 9 is a flowchart of a method for charged particle tracking (step 612 of FIG. 6). The method begins in step 902 where the radiation transport module 310 tracks all charged particles passing through the dosel grid 108. Next, in step 904, the radiation transport module 310, for a charged particle outside of the dosel grid, identifies a location of the charged particle. The radiation transport module 310 calculates an energy value (E0) associated with the charged particle, in step 906. Next, in step 908, the radiation transport module 310 accesses the energy gradient grid and retrieves an energy value (E1) required for the charged particle to travel from the location and enter the dosel grid 108. In step 910, the radiation transport module 310 discontinues tracking the charged particle if E0 is less than E1. Next, in step 912, the radiation transport module 310 continues tracking the charged particle if E0 is greater than or equal to E1. After step 912, the process of charged particle tracking is complete.

While the present invention has been described with reference to a preferred embodiment, those skilled in the art will recognize that various modifications may be made. Variations upon and modifications to the preferred embodiment are provided by the present invention, which is limited only by the following claims.

What is claimed is:

1. A method for calculating a radiation dose received by a target mass, comprising the steps of:

inputting voxel volumes enclosing a first portion of the target mass;

defining dosel volumes which enclose a second portion of the target mass and overlap the first portion;

calculating common volumes between the dosel volumes and the voxel volumes;

identifying locations in the target mass of energy deposits; and calculating radiation doses received by the target mass within the dosel volumes.

2. The method of claim 1 wherein the calculating common volumes step includes the steps of:

shrinking a size of and increasing a total number of the dosel volumes so that the dosel volumes form a periodic repeating pattern with respect to the voxel volumes;

calculating periodic common volumes between a first period of the periodic repeating pattern and the voxel volumes; and reusing the periodic common volumes to calculate a next set of common volumes within a next period of the periodic repeating pattern.

3. The method of claim 1:

wherein the step of inputting includes the step of, inputting voxel mass densities corresponding to a density of the target mass within each of the voxel volumes; and further including the steps of, multiplying the common volumes by corresponding voxel mass densities to obtain incremental dosel masses; and adding the incremental dosel masses corresponding to the dosel volumes to obtain dosel masses.

4. The method of claim 1 wherein the identifying step includes the steps of:

ending tracking of incident uncharged particles, which leave the target mass;

ending tracking of incident uncharged particles, which interact with the target mass;

identifying locations of incident uncharged particle interactions; and identifying the energy deposits at the locations.

5. The method of claim 1 wherein the identifying step includes the steps of:

ending tracking of daughter uncharged particles formed within the dosel volumes, which leave the target mass;

ending tracking of daughter uncharged particles formed within the dosel volumes, which interact with the target mass;

identifying locations of daughter uncharged particle interactions; and identifying the energy deposits at the locations.

6. The method of claim 1 wherein the identifying step includes the steps of:

ending tracking of daughter uncharged particles formed outside of and heading toward the dosel volumes, which leave the target mass;

ending tracking of daughter uncharged particles formed outside of and heading toward the dosel volumes, which interact with the target mass;

identifying locations of daughter uncharged particle interactions; and identifying the energy deposits at the locations.

7. The method of claim 1 wherein the identifying step includes the step of:

tracking daughter uncharged particles formed outside of and heading away from the dosel volumes, which have survived a variance reduction technique.

8. The method of claim 1 wherein the identifying step includes the step of:

tracking daughter uncharged particles formed outside of and heading away from the dosel volumes, which have survived a Russian Rouletting.

9. The method of claim 1 wherein the identifying step includes the steps of:

tracking charged particles passing through the dosel volumes;

defining a set of locations along a path of each of the charged particles; and assigning the energy deposits to the set of locations.

10. The method of claim 1 wherein the identifying step includes the steps of:

identifying locations of charged particles outside of the dosel volumes;

calculating a first set of energy values associated with the charged particles;

calculating a second set of energy values required for the charged particles to reach the dosel volumes; and ending tracking of a charged particle within the charged particles if an energy value corresponding to the charged particle in the first set is less than an energy value corresponding to the charged particle in the second set.

11. The method of claim 1 wherein the identifying step includes the steps of:

identifying locations of charged particles outside of the dosel volumes;

calculating a first set of energy values associated with the charged particles;

calculating a second set of energy values required for the charged particles to reach the dosel volumes; and tracking a charged particle within the charged particles if an energy value corresponding to the charged particle in the first set is not less than an energy value corresponding to the charged particle in the second set.

12. The method of claim 1 wherein the identifying step includes the steps of:

identifying a set of voxel volumes which do not overlap the dosel volumes;

calculating an energy value required for a charged particle to move from each voxel volume in the set of voxel volumes into the dosel volumes; and assigning the energy value to the voxel volume.

13. A system for calculating a radiation dose received by a target mass, comprising:

means for inputting voxel volumes enclosing a first portion of the target mass;

means for defining dosel volumes which enclose a second portion of the target mass and overlap the first portion;

means for calculating common volumes between the dosel volumes and the voxel volumes;

means for identifying locations in the target mass of energy deposits; and means for calculating radiation doses received by the target mass within the dosel volumes.

14. The system of claim 13 wherein the means for calculating common volumes includes:

means for shrinking a size of and increasing a total number of the dosel volumes so that the dosel volumes form a periodic repeating pattern with respect to the voxel volumes;

means for calculating periodic common volumes between a first period of the periodic repeating pattern and the voxel volumes; and means for reusing the periodic common volumes to calculate a next set of common volumes within a next period of the periodic repeating pattern.

15. The system of claim 13:

wherein the means for inputting includes, means for inputting voxel mass densities corresponding to a density of the target mass within each of the voxel volumes; and further including, means for multiplying the common volumes by corresponding voxel mass densities to obtain incremental dosel masses; and means for adding the incremental dosel masses corresponding to the dosel volumes to obtain dosel masses.

16. The system of claim 13 wherein the means for identifying includes:

means for ending tracking of incident uncharged particles, which leave the target mass;

means for ending tracking of incident uncharged particles, which interact with the target mass;

means for identifying locations of incident uncharged particle interactions; and means for identifying the energy deposits at the locations.

17. The system of claim 13 wherein the means for identifying includes:

means for ending tracking of daughter uncharged particles formed within the dosel volumes, which leave the target mass;

means for ending tracking of daughter uncharged particles formed within the dosel volumes, which interact with the target mass;

means for identifying locations of daughter uncharged particle interactions; and means for identifying the energy deposits at the locations.

18. The system of claim 13 wherein the means for identifying includes:

means for ending tracking of daughter uncharged particles formed outside of and heading toward the dosel volumes, which leave the target mass;

means for ending tracking of daughter uncharged particles formed outside of and heading toward the dosel volumes, which interact with the target mass;

means for identifying locations of daughter uncharged particle interactions; and means for identifying the energy deposits at the locations.

19. The system of claim 13 wherein the means for identifying includes:

means for tracking daughter uncharged particles formed outside of and heading away from the dosel volumes, which have survived a variance reduction technique.

20. The system of claim 13 wherein the means for identifying includes:

means for tracking daughter uncharged particles formed outside of and heading away from the dosel volumes, which have survived a Russian Rouletting.

21. The system of claim 13 wherein the means for identifying includes:

means for tracking charged particles passing through the dosel volumes;

means for defining a set of locations along a path of each of the charged particles; and means for assigning the energy deposits to the set of locations.

22. The system of claim 13 wherein the means for identifying includes:

means for identifying locations of charged particles outside of the dosel volumes;

means for calculating a first set of energy values associated with the charged particles;

means for calculating a second set of energy values required for the charged particles to reach the dosel volumes; and means for ending tracking of a charged particle within the charged particles if an energy value corresponding to the charged particle in the first set is less than an energy value corresponding to the charged particle in the second set.

23. The system of claim 13 wherein the means for identifying includes:

means for identifying locations of charged particles outside of the dosel volumes;

means for calculating a first set of energy values associated with the charged particles;

means for calculating a second set of energy values required for the charged particles to reach the dosel volumes; and means for tracking a charged particle within the charged particles if an energy value corresponding to the charged particle in the first set is not less than an energy value corresponding to the charged particle in the second set.

24. The system of claim 13 wherein the means for identifying includes:
   means for identifying a set of voxel volumes which do not overlap the dosel volumes;
   means for calculating an energy value required for a charged particle to move from each voxel volume in the set of voxel volumes into the dosel volumes; and
   means for assigning the energy value to the voxel volume.

25. A computer-usable medium embodying computer program code for causing a computer to calculate a radiation dose received by a target mass, by performing the steps of:
   inputting voxel volumes enclosing a first portion of the target mass;
   defining dosel volumes which enclose a second portion of the target mass and overlap the first portion;
   calculating common volumes between the dosel volumes and the voxel volumes;
   identifying locations in the target mass of energy deposits; and
   calculating radiation doses received by the target mass within the dosel volumes.

26. The computer-usable medium of claim 25 wherein the calculating common volumes step includes the steps of:
   shrinking a size of and increasing a total number of the dosel volumes so that the dosel volumes form a periodic repeating pattern with respect to the voxel volumes;
   calculating periodic common volumes between a first period of the periodic repeating pattern and the voxel volumes; and
   reusing the periodic common volumes to calculate a next set of common volumes within a next period of the periodic repeating pattern.

27. The computer-usable medium of claim 25:
   wherein the step of inputting includes the step of,
      inputting voxel mass densities corresponding to a density of the target mass within each of the voxel volumes; and
   further including the steps of,
      multiplying the common volumes by corresponding voxel mass densities to obtain incremental dosel masses; and
      adding the incremental dosel masses corresponding to the dosel volumes to obtain dosel masses.

28. The computer-usable medium of claim 25 wherein the identifying step includes the steps of:
   ending tracking of incident uncharged particles, which leave the target mass;
   ending tracking of incident uncharged particles, which interact with the target mass;
   identifying locations of incident uncharged particle interactions; and
   identifying the energy deposits at the locations.

29. The computer-usable medium of claim 25 wherein the identifying step includes the steps of:
   ending tracking of daughter uncharged particles formed within the dosel volumes, which leave the target mass;
   ending tracking of daughter uncharged particles formed within the dosel volumes, which interact with the target mass;
   identifying locations of daughter uncharged particle interactions; and
   identifying the energy deposits at the locations.

30. The computer-usable medium of claim 25 wherein the identifying step includes the steps of:
   ending tracking of daughter uncharged particles formed outside of and heading toward the dosel volumes, which leave the target mass;
   ending tracking of daughter uncharged particles formed outside of and heading toward the dosel volumes, which interact with the target mass;
   identifying locations of daughter uncharged particle interactions; and
   identifying the energy deposits at the locations.

31. The computer-usable medium of claim 25 wherein the identifying step includes the step of:
   tracking daughter uncharged particles formed outside of and heading away from the dosel volumes, which have survived a variance reduction technique.

32. The computer-usable medium of claim 25 wherein the identifying step includes the step of:
   tracking daughter uncharged particles formed outside of and heading away from the dosel volumes, which have survived a Russian Rouletting.

33. The computer-usable medium of claim 25 wherein the identifying step includes the steps of:
   tracking charged particles passing through the dosel volumes;
   defining a set of locations along a path of each of the charged particles; and
   assigning the energy deposits to the set of locations.

34. The computer-usable medium of claim 25 wherein the identifying step includes the steps of:
   identifying locations of charged particles outside of the dosel volumes;
   calculating a first set of energy values associated with the charged particles;
   calculating a second set of energy values required for the charged particles to reach the dosel volumes; and
   ending tracking of a charged particle within the charged particles if an energy value corresponding to the charged particle in the first set is less than an energy value corresponding to the charged particle in the second set.

35. The computer-usable medium of claim 25 wherein the identifying step includes the steps of:
   identifying locations of charged particles outside of the dosel volumes;
   calculating a first set of energy values associated with the charged particles;
   calculating a second set of energy values required for the charged particles to reach the dosel volumes; and
   tracking a charged particle within the charged particles if an energy value corresponding to the charged particle in the first set is not less than an energy value corresponding to the charged particle in the second set.

36. The computer-usable medium of claim 25 wherein the identifying step includes the steps of:
   identifying a set of voxel volumes which do not overlap the dosel volumes;
   calculating an energy value required for a charged particle to move from each voxel volume in the set of voxel volumes into the dosel volumes; and
   assigning the energy value to the voxel volume.

37. A system for calculating a radiation dose received by a target mass, comprising:

a common volume calculation module, for inputting voxel volumes enclosing a first portion of the target mass, defining dosel volumes which enclose a second portion of the target mass and overlap the first portion, and calculating common volumes between the dosel volumes and the voxel volumes;

a radiation transport module, coupled to the common volume calculation module, for identifying locations in the target mass of energy deposits; and a dose calculation module, coupled to the common volume calculation module and the radiation transport module, for calculating radiation doses received by the target mass within the dosel volumes.

38. The system of claim 37, further comprising:

a dosel mass module, coupled to receive voxel mass densities corresponding to a density of the target mass within each of the voxel volumes and coupled to the dose calculation module, for multiplying the common volumes by corresponding voxel mass densities to obtain incremental dosel masses, and adding the incremental dosel masses corresponding to the dosel volumes to obtain dosel masses.

39. A method for calculating a common volume, comprising the steps of:

inputting a spherical dosel volume of radius (r) enclosing a first portion of a target mass;

defining an (x, y, z) coordinate system with an origin at a center of the spherical dosel volume;

normalizing x, y, and z in terms of the radius (r);

inputting a rectangular parallelepiped voxel volume which encloses a second portion of the target mass and overlaps the spherical dosel volume;

dividing the rectangular voxel volume into rectangular sub-voxel volumes such that each sub-voxel has a set of corners and is located in one octant of the spherical dosel volume;

selecting a sub-voxel volume located in an octant of the spherical dosel volume where x, y, and z are each positive and having a corner (x0, y0, z0) located closest to the origin of the spherical dosel volume;

defining a corner volume, V3(x, y, z), located at a point (x, y, z) and bounded by an x-y plane that goes through (x, y, z), an x-z plane that goes through (x, y, z), a y-z plane that goes through (x, y, z), and a portion of a surface of the spherical dosel volume which is located entirely within the octant in which (x, y, z) is located;

identifying a width for each side of the rectangular sub-voxel volume as dx, dy, dz; and calculating a common volume between the rectangular sub-voxel volume and the spherical dosel volume within as, $$V = V3(x0, y0, z0) - \begin{bmatrix} V3(x0+dx, y0, z0) + \\ V3(x0, y0+dy, z0) + \\ V3(x0, y0, z0+dz) \end{bmatrix} + \begin{bmatrix} V3(x0+dx, y0+dy, z0) + \\ V3(x0+dx, y0, z0+dz) + \\ V3(x0, y0+dy, z0+dz) \end{bmatrix} - V3(x0+dx, y0+dy, z0).$$

40. The method of claim 39, wherein the step of defining a corner volume comprises the step of:

calculating the corner volume, V3(x, y, z) as, $$V3(x, y, z) = \frac{r^3}{6} \left\{ \begin{array}{l} g(x, y, z) + \\ f(x, y) + f(x, z) + f(y, z) \end{array} \right\}$$

where, $$g(x, y, z) = -2\pi - 6xyz + \frac{\pi}{2}\{x(3-x^2) + y(3-y^2) + z(3-z^2)\}$$

and, $$f(x, y) = 2xy\sqrt{1-x^2-y^2} + 2\text{ArcTan}\left(\frac{\sqrt{1-x^2-y^2}}{xy}\right) -$$

$$x(3-x^2)\text{ArcTan}\left(\frac{\sqrt{1-x^2-y^2}}{y}\right) -$$

$$y(3-y^2)\text{ArcTan}\left(\frac{\sqrt{1-x^2-y^2}}{x}\right).$$

41. A method for calculating an energy gradient grid, comprising the steps of:

calculating a minimum kinetic energy for a dosel grid and a first shell of voxels outside of the dosel grid such that a corresponding CSDA range is predetermined multiple of a minimum dimension of a voxel within the first shell of voxels;

growing paths out from each voxel in the first shell of voxels to an adjacent voxel in a second shell of voxels; and raster scanning the second shell of voxels.

* * * * *